US00PP20734P2

(12) United States Plant Patent
Saul

(10) Patent No.: US PP20,734 P2
(45) Date of Patent: Feb. 9, 2010

(54) ***AJUGA* PLANT NAMED 'MINT CHIP'**

(50) Latin Name: *Ajuga×tenorii*
Varietal Denomination: Mint Chip

(75) Inventor: Richard G. Saul, Cleveland, GA (US)

(73) Assignee: Itsaul Plants, LLC., Alpharetta, GA (US)

( * ) Notice: Subject to any disclaimer, the term of this patent is extended or adjusted under 35 U.S.C. 154(b) by 0 days.

(21) Appl. No.: 12/288,808

(22) Filed: Oct. 23, 2008

(51) Int. Cl.
*A01H 5/00* (2006.01)

(52) U.S. Cl. ..... Plt./401

(58) Field of Classification Search ..... Plt./401
See application file for complete search history.

*Primary Examiner*—June Hwu
(74) *Attorney, Agent, or Firm*—Penny J. Aguirre

(57) ABSTRACT

A new cultivar of *Ajuga* plant, 'Mint Chip', characterized by its foliage that is deep green in color with a glossy surface, its heavy blooming habit of blue flowers present for 4 to 6 weeks in spring that contrast well with the deep green foliage, its very vigorous growth habit, and its tight plant habit that slowly spreads by stolons with suitability as a groundcover.

2 Drawing Sheets

Botanical classification: *Ajuga×tenorii.*
Variety denomination: 'Mint Chip'.

BACKGROUND OF THE INVENTION

The present invention relates to a new and distinct cultivar of *Ajuga* plant, botanically known as *Ajuga×tenorii* 'Mint Chip' and will be referred to hereinafter by its cultivar name, 'Mint Chip'. The new cultivar of *Ajuga* is a hardy herbaceous perennial grown for landscape use.

'Mint Chip' was discovered in March of 2005 as a naturally occurring meristematic mutation of *Ajuga×tenorii* 'Chocolate Chip' (not patented) in a container in his nursery in Dahlonega, Ga.

Asexual reproduction of the new cultivar was first accomplished by basal stem cuttings in June of 2005 in Alpharetta, Ga. Propagation by cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Mint Chip' as a unique cultivar of *Ajuga.*

1. 'Mint Chip' exhibits foliage that is deep green in color with a glossy surface.
2. 'Mint Chip' is a heavy bloomer with an abundance of blue flowers present for 4 to 6 weeks in April and May in Georgia.
3. 'Mint Chip' exhibits a unique combination of foliage and flowers with the high contrast between the deep green foliage and blue flowers.
4. 'Mint Chip' exhibits a very vigorous growth rate.
5. 'Mint Chip' exhibits a tight plant habit and slowly spreads by stolons with suitability as a groundcover.

The parent plant, 'Chocolate Chip', differs from 'Mint Chip' in having mature foliage that is dark green to brown with new foliage that emerges deep green with a burgundy flush thus having foliage that has a darker overall appearance and in having a slower growth rate. 'Mint Chip' can also be compared to the cultivar 'Emerald Chip' (Not patented) for its similarity in leaf size, plant size and green foliage. 'Mint Chip' differs from 'Emerald Chip' in having a much heavier blooming habit.

BRIEF DESCRIPTION OF THE DRAWINGS

The accompanying colored photographs illustrate the overall appearance and distinct characteristics of the new *Ajuga*. The photographs in the figures were taken of two year-old plants as grown outdoors in a one-gallon containers in Alpharetta, Ga.

The photograph in FIG. 1 provides a view of 'Mint Chip' in bloom with the contrast between the foliage and flowers illustrated.

Figure 1:
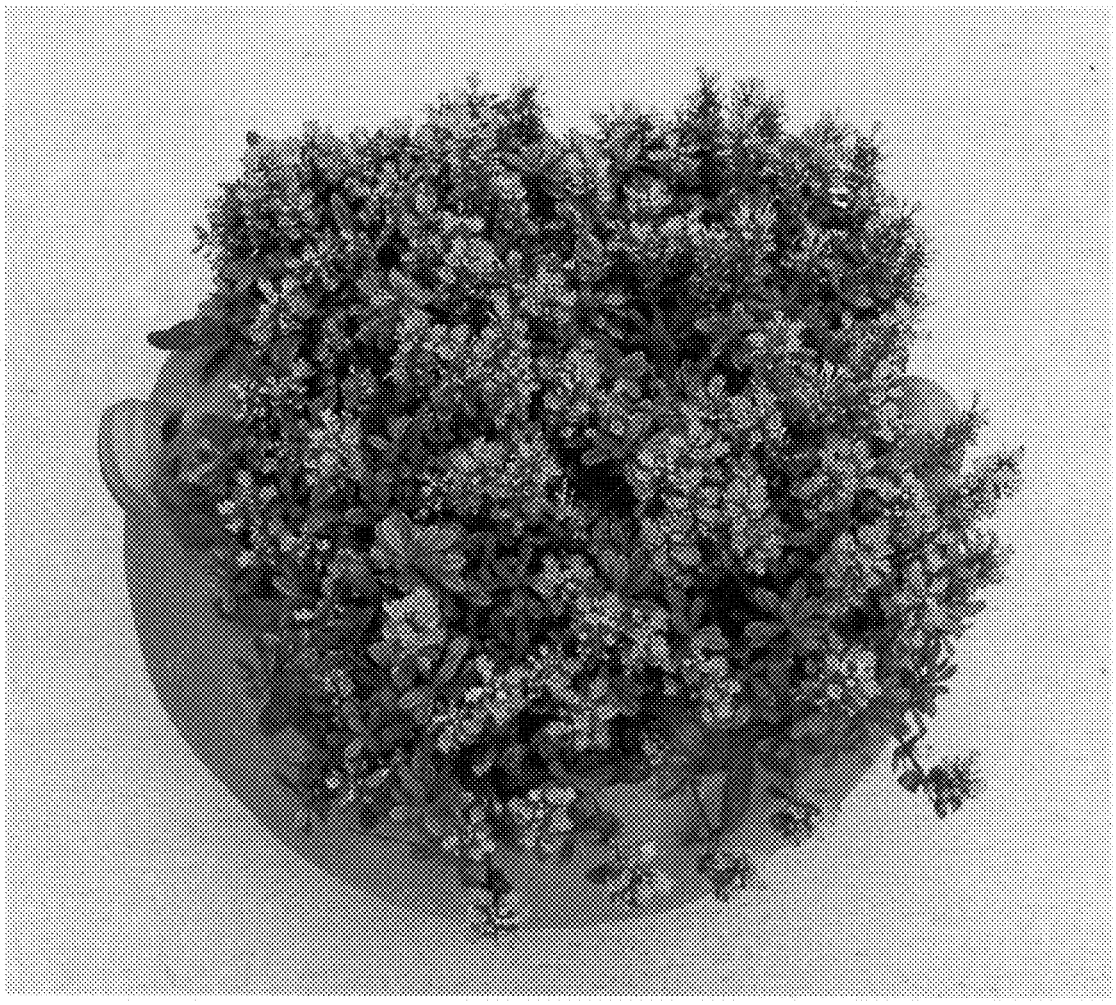
Figure 2:
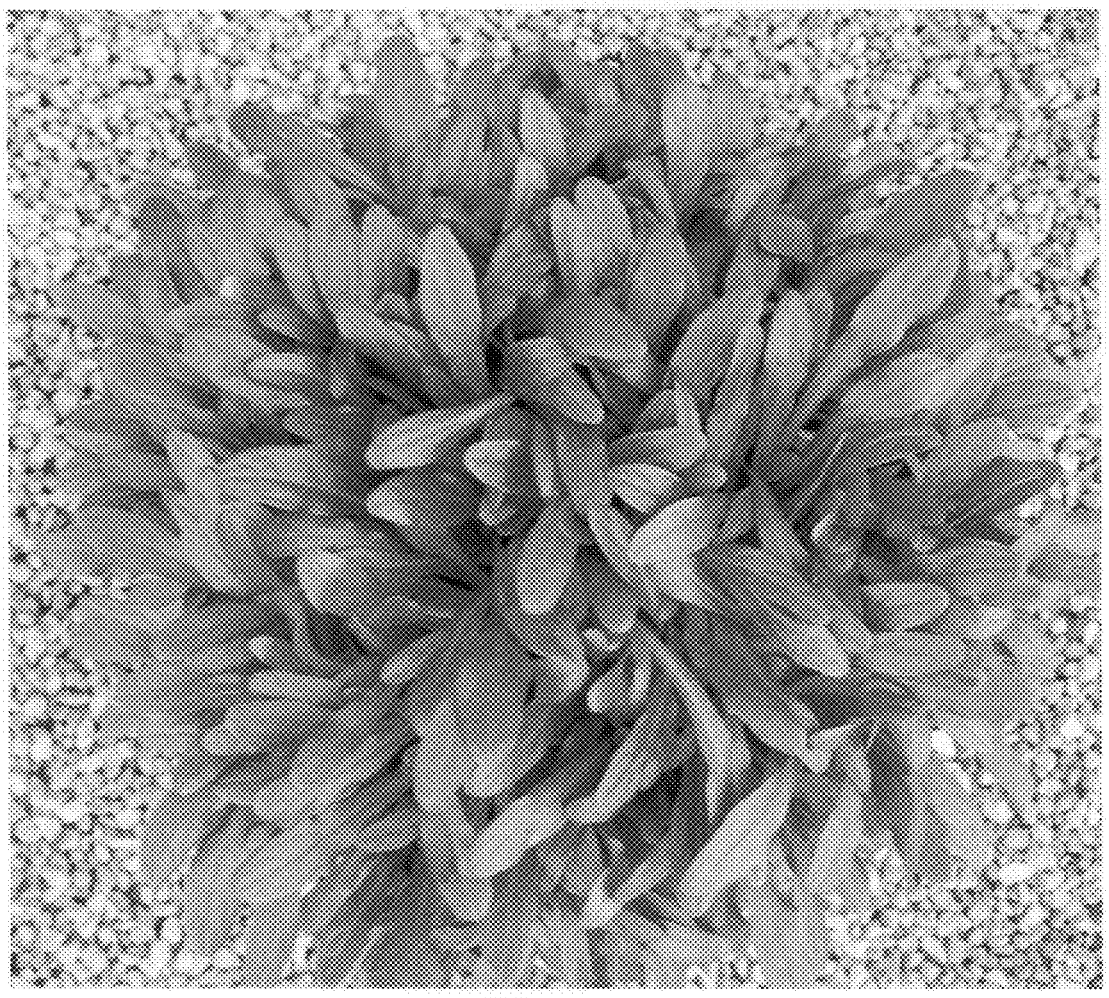

The photograph in FIG. 2 provides a close-up view of the foliage of 'Mint Chip'.

The colors in the photograph may differ slightly from the color values cited in the detailed botanical description, which accurately describe the colors of the new *Ajuga.*

DETAILED BOTANICAL DESCRIPTION

The following is a detailed description of the new cultivar as observed for two years in the garden in Alpharetta, Ga. with the detailed botanical data collected from one year-old plants as grown outdoors in 2-quart containers in Alpharetta, Ga. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Plant habit.*—Compact, herbaceous perennial, mounded foliage, slowly spreading by stolons.

*Blooming period.*—Spring blooming for 4 to 6 weeks in April and May in Georgia.

*Height and spread.*—Reaches about a height of about 5 cm in height and about 15 cm in width in a one-gallon container.

*Cold hardiness.*—U.S.D.A. Zones 5 to 9.

*Diseases and pests.*—Observed to be highly disease and pest resisitant.

*Root description.*—Fibrous roots on short rhizomes, roots 158D in color, rhizomes about 1.5 cm in length and 3.5 mm in width.

*Stolons.*—146B suffused with 187C in color and an average of 3.5 cm in length and 1.5 mm in width.

*Branching habit.*—Basal rosettes of leaves from rhizomes.

*Propagation.*—Cutting and division.

*Root initiation.*—Roots appear in rooting media in 7 days at 75° F. under mist in greenhouse conditions.

*Root development.*—Cuttings root and fully develop in a 72 cell plug in 4 to 5 weeks in all seasons under greenhouse conditions without supplemental lighting.

*Growth rate.*—Very vigorous.

Foliage description:

*Leaf shape.*—Spatulate.

*Leaf division.*—Simple.

*Leaf base.*—Truncate to base of rhizome.

*Leaf apex.*—Broadly acute to rounded.

*Leaf venation.*—Pinnate, 144C on upper and lower surface, only base of midrib on both surfaces is conspicuous.

*Leaf margins.*—Entire.

*Leaf attachment and arrangement.*—2-ranked from rhizome.

*Leaf orientation.*—Emerge upright and then slightly recurve.

*Leaf surface.*—Finely puberulent on upper and lower surface, slightly satiny on upper surface and dull on lower surface.

*Leaf color.*—Upper surface, newly emerged foliage; 137A to 137B, lower surface, color between 138A and 146B, mature foliage upper surface; N189A, mature foliage lower surface; 137A to 137B with puberulent covering of 194B.

*Leaf size.*—Mature to about 6.3 cm and 1.8 cm in width.

*Leaf quantity.*—Average of 30 per rhizome and about 500 per 2-quart container.

*Leaf attachment.*—Sessile.

Flower description:

*Inflorescence type.*—Raceme of dense whorls of bilabiate flowers.

*Inflorescence size.*—An average of 14 cm in height and 2.2 cm in width.

*Inflorescence number.*—An average of 80 per plant as grown in a one-gallon container.

*Lastingness of inflorescence.*—Individual flowers last 2 to 3 days.

*Flower type.*—Bilabiate.

*Flower number.*—About 2 to 6 flowers per whorl, about 40 per raceme.

*Flower fragrance.*—None.

*Flower buds.*—Oblong in shape, about 4 mm in length and 2.5 mm in diameter, villose surface, color of apex is a blend of 97A and 97C, color of calyx portion 138B.

*Flower buds.*—Oblong in shape, about 4 mm in length and 2.5 mm in diameter, villose surface, color of apex is a blend of 97A and 97C, color of calyx portion 138B.

*Flower size.*—About 1.2 cm in length and about 7 mm in diameter.

*Peduncles.*—An average of 14 cm in length and 3 mm in width, color is a blend of 138A and 138B, surface is villose.

*Pedicels.*—None, sessile.

*Calyx.*—5-pointed, star-shaped, about 25 mm in length and 3 mm in width, persistent but dries.

*Sepals.*—5, elliptic in shape, about 1.5 mm in width and 2.5 mm in length, 138B in color on both surfaces, pubescent on both surfaces, margin is entire and villose.

*Petals.*—2 segments with shorter upper lip and a spreading lower lip with both segment fused into tube that is about 6 mm in length and 1 to 2 mm in width, upper lip has 2 oblanceolate shaped lobes fused together with apex free and acute with free portion about 1 mm in length and 2 mm in width, lower lip has 4 lobes; 2 oblong side lobes that spread sideways and are slightly reflexed with a broadly acute apex with free portion about 4 mm in length and 1.5 mm in width and 2 center lobes that are oblanceote in shape and slightly reflexed with a rounded apex and with free portion about 6 mm in length and 2.5 mm in width, all segments have entire margins, are pubescent on the outer surfaces and glabrous and satiny on the inner surfaces, color of inner surfaces is 96B to 96C with stripes of 97C to 97D, color of tube and outer surfaces is a blend of 91A, 91B and 91C.

*Bracts.*—Average of 2 per whorl, an average of 1.1 cm in length and 9 mm in width, elliptic in shape, sessile, acute apex, truncate base, finely puberulent on both upper and lower surface, color N189A on upper surface and 137B on lower surface.

Reproductive Organs:

*Pistils.*—1, style with stigma is about 9 mm in length, 0.5 mm in width and 91D in color and translucent.

*Stamens.*—4, filament is about 7 mm in length, 0.3 mm in width and 91D in color, anthers are oblong in shape and 203B in color, pollen is moderate in quantity and 15B in color.

*Fruit.*—Fruit and seed production was not observed under the conditions tested.

It is claimed:

1. A new and distinct variety of *Ajuga* plant named 'Mint Chip' as described and illustrated herein.

* * * * *